United States Patent
Asakawa et al.

(10) Patent No.: US 6,642,350 B1
(45) Date of Patent: Nov. 4, 2003

(54) METHOD OF PURIFYING BISHYDROXYALKYL TEREPHTHALATE

(75) Inventors: Yuji Asakawa, Tokyo (JP); Shin Asano, Tokyo (JP)

(73) Assignees: Organo Corporation (JP); Aies Co., Ltd. (JP)

( * ) Notice: Subject to any disclaimer, the term of this patent is extended or adjusted under 35 U.S.C. 154(b) by 0 days.

(21) Appl. No.: 10/111,785

(22) PCT Filed: May 24, 2000

(86) PCT No.: PCT/JP00/03316
§ 371 (c)(1),
(2), (4) Date: Apr. 26, 2002

(87) PCT Pub. No.: WO01/32597
PCT Pub. Date: May 10, 2001

(30) Foreign Application Priority Data

Oct. 28, 1999 (JP) ............................................. 11-306723

(51) Int. Cl.[7] ............................. C08F 6/00; C08J 11/04; B01D 11/00
(52) U.S. Cl. ...................... 528/482; 521/48; 521/48.5; 528/490; 528/491; 528/495; 528/502; 528/503; 210/633; 210/635; 210/638; 210/660
(58) Field of Search .................. 521/48, 48.5; 528/482, 528/490, 491, 495, 502, 503; 210/633, 635, 638, 660

(56) References Cited

FOREIGN PATENT DOCUMENTS

| EP | 1 120 394 A1 | 8/2001 |
|---|---|---|
| JP | 47-10379 | 3/1972 |
| JP | 50-71639 | 6/1975 |
| JP | 60-72845 | 4/1985 |
| JP | 2000-159729 | 6/2000 |
| JP | 2000-191593 | 7/2000 |

OTHER PUBLICATIONS

Patent Abstracts of Japan, publication No. 2000159729A, published Jun. 13, 2000 (1 Page).
Patent Abstracts of Japan, publication No. 2000191593A, published Jul. 11, 2000 (1 page).
Patent Abstracts of Japan, publication No. 60072845A, published Apr. 24, 1985 (1 page).
International Search Report dated Mar. 14, 2003 (3 page).

*Primary Examiner*—Samuel A. Acquah
(74) *Attorney, Agent, or Firm*—Rosenthal & Osha L.L.P.

(57) ABSTRACT

A container made of, e.g., polyethylene terephthalate is pulverized and decomposed in the presence of a catalyst by the use of a solvent such as an alcohol or glycol to obtain crude bishydroxyalkyl terephthalate. This crude bishydroxyalkyl terephthalate is then purified by filtration, a treatment with activated carbon, and a treatment with ion-exchange resins. The bishydroxyalkyl terephthalate thus obtained is condensed to produce a container or the like made of polyethylene terephthalate.

26 Claims, 2 Drawing Sheets

METHOD OF PURIFYING BISHYDROXYALKYL TEREPHTHALATE

TECHNICAL FIELD

The present invention relates to a method of purifying bishydroxyalkyl terephthalate. More specifically, the present invention relates to a method of purifying crude bishydroxyalkyl terephthalate usable as a material for polyalkylene terephthalate such as recycled polyethylene terephthalate or polybutylene terephthalate.

BACKGROUND ART

Heretofore, polyalkylene terephthalate (hereinafter abbreviated as "PET or the like") such as polyethylene terephthalate or polybutylene terephthalate is produced by causing dimethyl terephthalate or terephthalic acid to react with ethylene glycol or 1,4-butanediol to produce bishydroxyethyl terephthalate or bishydroxybutyl terephthalate (hereinafter abbreviated as "BHET or the like") and condensing BHET or the like. In this case, since crude BHET or the like obtained from dimethyl terephthalate or terephthalic acid contains methanol or water as a by-product, crude BHET or the like is purified by distillation to remove methanol or water therefrom before condensation.

Meanwhile, in Japan, a container and package recycling law has been in effect since April in 1997, and demand for recycling PET or the like has been increasing. As methods for recycling PET or the like, a method in which recovered PET or the like is shredded, molten and processed into fibrous PET or the like which is used as fabric and a chemical recycle method in which recovered PET or the like is decomposed into raw material monomers (such as BHET or the like), which are recovered and PET or the like is synthesized again from the recovered monomers.

As a chemical recycle method for PET or the like, a method is known in which PET or the like is decomposed by solvolysis using a solvent such as an alcohol or glycol in the presence of a catalyst to recover monomers (such as BHET or the like) are recovered.

However, monomers (such as BHET or the like) recovered by the chemical recycle methods contain a variety of by-products produced by decomposition, colorants, adherent substances, and impurities such as ions contained in water used during the recycling process. Synthesis of PET or the like requires use of highly purified monomers. Since monomers recovered by the chemical recycle methods contain a large amount of impurities, these monomers as such cannot be used for the synthesis of PET or the like.

It is an object of the present invention is to provide a method of purifying bishydroxyalkyl terephthalate which is capable of obtaining highly purified monomers usable in synthesis of PET or the like.

DISCLOSURE OF THE INVENTION

The present invention is characterized in that crude bishydroxyalkyl terephthalate is treated with activated carbon and ion exchange resins to purify it.

Further, in another embodiment, the above treatment with activated carbon and ion exchange resins in the present invention comprises a solution passing step in which a solution containing crude bishydroxyalkyl terephthalate is passed through an activated carbon column filled with activated carbon and ion exchange resin columns filled with ion exchange resins, and an sweetening-off step in which ethylene glycol or an alcohol as a solvent is passed through each column after the solution passing step to displace bishydroxyalkyl terephthalate.

Further, in still another embodiment, the above treatment with the ion exchange resins in the present invention comprises a step of passing the solution through a single bed of a strongly acidic cation exchange resin and a step of passing the solution through a mixed bed of a strongly acidic cation exchange resin and a weakly basic anion exchange resin.

Further, in still another embodiment, the present invention has a filtration step which is carried out prior to the above treatment with activated carbon and ion exchange resin(s). The filtration is carried out at a temperature higher than a temperature at which the treatment with activated carbon and ion exchange resins is carried out by 5° C. or lower.

Further, in still another embodiment, the present invention comprises a depolymerization step in which polyalkylene terephthalate is subjected to ester depolymerization to produce crude bishydroxyalkyl terephthalate and a purification step in which the obtained crude bishydroxyalkyl terephthalate is filtered and then purified and returns a solid separated by the filtration in the above purification step to the above depolymerization step.

BEST MODES FOR CARRYING OUT THE INVENTION

First Embodiment

Figure 1:
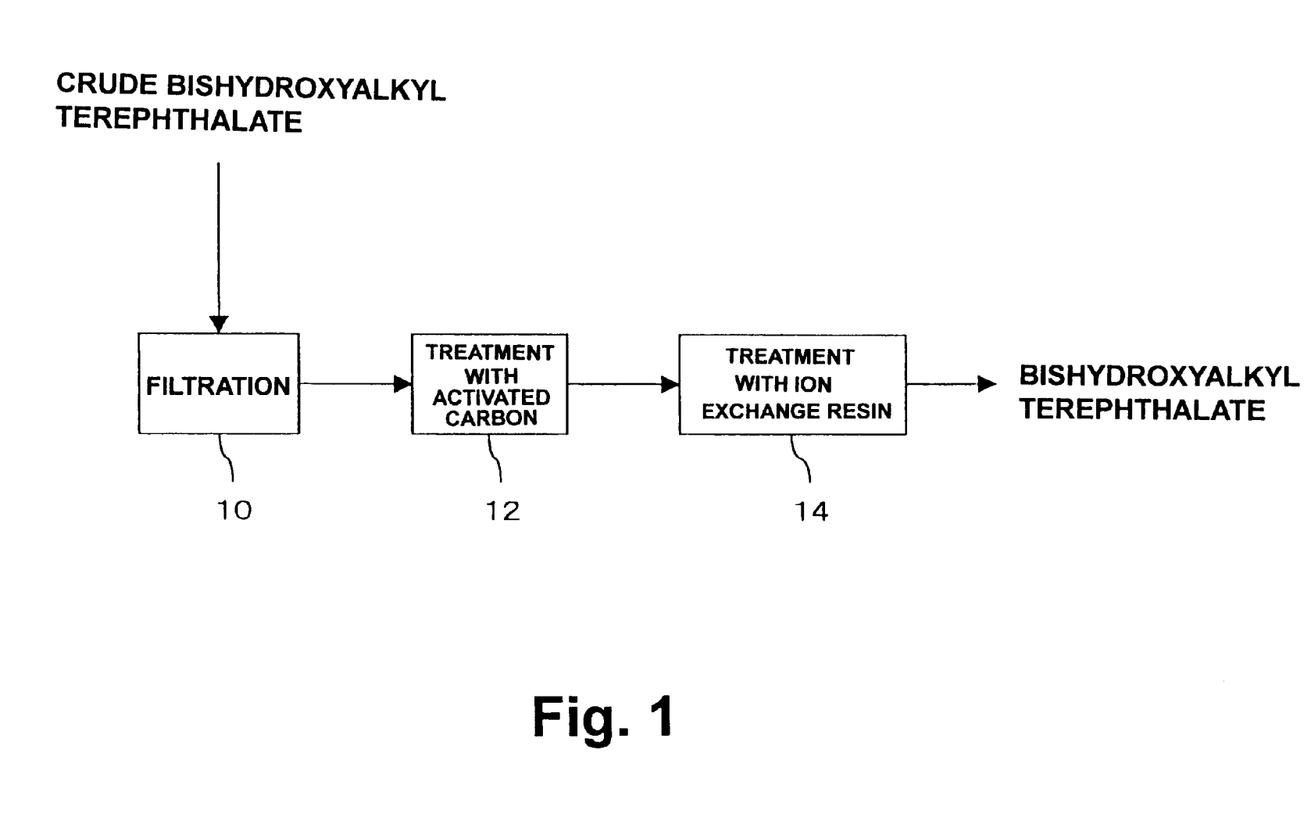
FIG. 1 is a diagram of showing the constitution of first to fourth embodiments.

FIG. 1 shows the overall constitution of the first embodiment in which bishydroxyalkyl terephthalate is purified from PET or the like.

Crude bishydroxyalkyl terephthalate (hereinafter referred to as "crude BHET") is supplied to filtration 10 where solids are removed. Then, the filtered crude BHET is supplied to activated carbon treatment 12 where the BHET is passed through an activated carbon bed to carry out activated carbon adsorption treatment. Thereafter, the resulting BHET is supplied to ion exchange resin treatment 14 where ions are removed from the BHET.

When crude BHET is purified by concurrent use of activated carbon and ion exchange resins as described above, colorants and impurity ions contained in crude BHET can be removed efficiently. Thereafter, purified BHET or the like can be used as a raw material monomer for recycled PET or the like.

The crude BHET or the like to be treated may be crude BHET or the like obtained in a chemical recycle process of waste PET or the like as well as crude BHET or the like obtained from dimethyl terephthalate or terephthalic acid which is a high-purity raw material used in the synthesis of ordinary PET or the like.

As the chemical recycle process of PET or the like, any process which is capable of decomposing PET or the like into crude BHET or the like may be used. For example, a solvolysis process of PET or the like using a solvent or a decomposition process using a supercritical solution may be used.

Since crude BHET or the like obtained by decomposition in the chemical recycle process contains polymerization catalysts for PET and inorganic pigments as insoluble inorganic impurities, the insoluble inorganic impurities must be removed by means of a ceramic filter or the like before purification is performed.

Further, although a detailed removal mechanism for purifying crude BHET or the like is not known, it has been found that colorants contained in crude BHET or the like are not adsorbed well by ion exchange resins but adsorbed by activated carbon. Illustrative examples of usable activated carbon include coal-based activated carbon and wood-based activated carbon. Of these activated carbons, wood-based activated carbon is preferred from the viewpoints of the effect of removing colorants and resistance to heat used for its regeneration. A temperature at which a solution of crude BHET or the like is passed through activated carbon is 40 to 180° C., preferably 60 to 100° C. When this temperature is lower than 40° C., although depending on the concentration of BHET or the like, some portions remain undissolved disadvantageously. On the other hand, when this temperature is higher than 180° C., the temperature exceeds the boiling point of ethylene glycol or the like disadvantageously.

Further, it has also been found by studies made by the present inventors that both cation and anion components are contained in impurity ions of crude BHET or the like. It has been found that these impurity ions can be removed by dissolving crude BHET or the like in a solvent heated at 40 to 120° C., preferably 60 to 100° C., and then passing the resulting solution through an anion exchange resin and a cation exchange resin.

When the temperature is lower than 40° C., although depending on the concentration of BHET or the like, some portions remain undissolved disadvantageously. On the other hand, when it is higher than 140° C., life in terms of number of days of the ion exchange resins may be shortened disadvantageously.

When the temperature is higher than 70° C., life in terms of number of days of a strongly basic anion exchange resin is shortened. Therefore, use of a weakly basic anion exchange resin is preferred.

It is preferred that crude BHET or the like be treated after dissolving it in a solvent heated. Illustrative examples of a solvent to be used include methanol, or ethylene glycol or the like which is used in solvolysis of a PET or the like.

The ion exchange resins should be used in a conventionally known technique. Illustrative examples of such a technique include a multi-column technique, a mix-bed technique and a stratified bed technique. Particularly, when high purity is desired, a mix-bed column is preferred.

The treatment with activated carbon and the treatment with the ion exchange resins may be carried out in any order. However, since elution of oxides occurs by passing the solution through the activated carbon column depending on the degree of purity of activated carbon, it is preferred to carry out the treatment with the ion exchange resins after the treatment with activated carbon has been carried out.

(Examples About First Embodiment)

A crude BHET solution used in Examples and Comparative Examples was a solution which was obtained by filtration after a process of chemically recycling PET bottles and which comprised 18 wt % of BHET, 81 wt % of ethylene glycol and 1 wt % of water.

EXAMPLE 1

After a crude BHET solution was passed through an activated carbon column filled with 100 ml of wood activated coal ("TAIKO SGA" manufactured by Futamura Chemical Industries Co., Ltd.) at 60° C. and a flow rate of 250 ml/hr, the solution was passed through a mix-bed ion exchange resin bed (25 ml of the strongly basic anion exchange resin "AMBERRITE IRA-402BL"+25 ml of the strongly acidic cation exchange resin "AMBERRITE IR-120B", both manufactured by ROHM & HAAS COMPANY).

The crude BHET solution and the treated solution were subjected to conductivity measurement at 60° C., visual evaluation of color and absorbance determination using a 10-mm cell. The results are shown in Table 1.

EXAMPLE 2

After a crude BHET solution was passed through an activated carbon column filled with 100 ml of wood activated coal ("TAIKO SGA" manufactured by Futamura Chemical Industries Co., Ltd.) at 80° C. and a flow rate of 250 ml/hr, the solution was passed through two beds (25 ml of "AMBERRITE IR-120B"→25 ml of weakly basic anion exchange resin "AMBERRITE IRA-96SB").

The conductivity, color and absorbance of the treated solution were determined in the same manners as in Example 1. The results are shown in Table 1.

Comparative Example 1

A crude BHET solution was passed through an activated carbon column filled with 100 ml of wood-based activated carbon ("TAIKO SGA" manufactured by Futamura Chemical Industries Co., Ltd.) at 80° C. and a flow rate of 250 ml/hr.

The conductivity, color and absorbance of the treated solution were determined in the same manners as in Example 1. The results are shown in Table 1.

Comparative Example 2

A crude BHET solution was passed through a mix-bed ion exchange resin bed (25 ml of "AMBERRITE IRA-402B"+25 ml of "AMBERRITE IR-120B") at 60° C. and a flow rate of 250 ml/hr.

The conductivity, color and absorbance of the treated solution were determined in the same manners as in Example 1. The results are shown in Table 1.

TABLE 1

| Solution | Conductivity ($\mu$S/cm) | Color | Absorbance (675 nm) | Absorbance (420 nm) |
| --- | --- | --- | --- | --- |
| Crude BHET Solution | 205 | Cloudy Green | 0.071 | 0.192 |
| Example 1 | 1.67 | Colorless Transparent | −0.001 | 0.018 |
| Example 2 | 2.50 | Colorless Transparent | −0.001 | 0.018 |
| Comparative Example 1 | 193 | Pale Yellow | 0.001 | 0.104 |
| Com. Example 2 | 1.73 | Green | 0.026 | 0.034 |

As is obvious from the results shown in Table 1, the conductivity of the treated solution in Comparative Example 1 was high since the purification method of Comparative Example 1 using only a treatment with activated carbon was carried out could not remove impurity ions, and the treated solution in Comparative Example 2 remained colored since the purification method of Comparative Example 2 in which only treatment with ion exchange resins was carried out could not adsorb colorants. On the other hand, the treated solutions of Examples 1 and 2 which underwent the treatment with activated carbon and the treatment with ion exchange resins were deprived of impurity ions and colorants.

As described above, according to the first embodiment, colorants and impurity ions contained in crude BHET and the like could be removed efficiently by subjecting the crude BHET or the like to purification using a combination of activated carbon and ion exchange resins. The purified BHET or the like can be used as a raw material monomer for recycled PET or the like.

Second Embodiment

Next, a second embodiment will be described. An overall process in the second embodiment is the same as that of the first embodiment, and description thereof will be omitted.

The method described in the above first embodiment is an effective method of purifying crude BHET or the like. An overall process in the second embodiment is the same as that of the first embodiment, and description thereof will be omitted.

However, ion exchange resins are normally regenerated with proper frequencies since ion exchange capacity is exhausted with use.

In the regeneration of the ion exchange resin(s), a sweetening-off step in which BHET or the like is displaced by use of hot water is carried out prior to the regeneration by use of regenerant chemicals. However, it has been found that when the sweetening-off is carried out by use of generally used hot water in the displacement step of the regeneration, BHET or the like is deposited during the sweetening-off step, so that water cannot pass through columns.

In the second embodiment, in a method of purifying bishydroxyalkyl terephthalate in which crude bishydroxyalkyl terephthalate is passed through a treatment system comprising a combination of an activated carbon column and an ion exchange resin column to purify it, ethylene glycol or an alcohol is used as a displacement solvent in the sweetening-off step after the crude bishydroxyalkyl terephthalate has been passed through both columns.

The displacement solvent used in the sweetening-off step of the second embodiment is ethylene glycol or an alcohol. Illustrative examples of the alcohol include methanol, ethanol and isopropanol. A preferred solvent is ethylene glycol or methanol.

By using ethylene glycol or an alcohol as the displacement solvent, the sweetening-off can be performed without having crude BHET in the ion exchange resin column and the activated carbon column deposited therein.

The concentration of ethylene glycol or an alcohol which is passed through the columns in the sweetening-off step is preferably not lower than 30% (aqueous solution). When the concentration of these displacement solvents is lower than 30%, crude BHET may be deposited in the ion exchange resin column and the activated carbon column undesirably.

An embodiment of the step of regenerating ion exchange resins by the method of the present invention is shown below.

(1) sweetening-off of crude BHET or the like with ethylene glycol or an alcohol
(2) displacement of ethylene glycol or an alcohol with hot water
(3) rinse of ion exchange resins with water
(4) regeneration by passing regenerant chemicals through the ion exchange resins
(5) displacement with water
(6) rinse of the ion exchange resins with water
(7) replacement of water with ethylene glycol or an alcohol
(8) passing crude BHET solution through the columns The ion exchange resins are rinsed with water (displacement with water) after the regenerant chemicals have been passed through the ion exchange resins. However, when crude BHET or the like is passed through the ion exchange resins after the ion exchange resins are rinsed with water, the crude BHET or the like is deposited in the column. Therefore, water in the column must be replaced with ethylene glycol or an alcohol before the crude BHET or the like is passed through the column.

A solution discharged from the sweetening-off step of the method of the present invention contains crude BHET or the like. This crude BHET or the like is preferably returned to the purification step using activated carbon and ion exchange resins to recover and reuse it.

In the case of activated carbon, it is regenerated by use of a furnace or a chemical.

(Example of Second Embodiment)

A crude BHET solution used in Example and Comparative Examples was a solution which was obtained by filtering the solution resulting from the process of chemically recycling PET bottles and comprised 18 wt % of BHET, 81 wt % of ethylene glycol and 1 wt % of water.

EXAMPLE 3

A crude BHET solution obtained from a process of chemically recycling PET bottles was treated. The crude BHET solution comprised 18% of BHET, 81% of ethylene glycol and 1% of water.

The raw solution to be treated was in the form of slurry at room temperature (25° C.) and could not be passed through an activated carbon column and an ion exchange resin column as it is. Therefore, it was heated to 55° C. or higher and passed through the columns.

The raw solution to be treated was passed through an activated carbon column filled with 100 ml of wood-based activated carbon ("TAIKO SGA" manufactured by Futamura Chemical Industries Co., Ltd.) and a mix-bed ion exchange resin column (25 ml of "AMBERRITE IRA-402BL"+25 ml of "AMBERRITE IR-120B", both manufactured by ROHM & HAAS COMPANY) at 60° C. in this order.

Thereafter, sweetening-off steps were carried out by use of hot water, ethylene glycol, methanol and isopropanol as displacement solvents. The conditions of the activated carbon column and the ion exchange resin column were observed visually after the sweetening-off step using each of the solvents. The results are shown in Table 2.

TABLE 2

| Displacement Solvents | Conditions |
| --- | --- |
| Hot Water at 60° C. | The liquid phase became clouded along with deposition of BHET or the like, and a white deposit was accumulated on the surface of the activated carbon bed. |
| Ethylene Glycol 99% | No BHET or the like was deposited, and the liquid phase was colorless and transparent |
| Ethylene | A small amount of BHET or the like was |

TABLE 2-continued

| Displacement Solvents | Conditions |
|---|---|
| Glycol 60% | deposited but was not accumulated on the surface of the activated carbon bed, and the liquid phase also became colorless and transparent thereafter. |
| Ethylene Glycol 30% | A large amount of BHET or the like was deposited, and deposition was seen on the surface of the activated carbon layer, but the accumulation became insoluble immediately. |
| Methanol | No BHET or the like was deposited, and the liquid phase was colorless and transparent. |
| Iso-propanol | No BHET or the like was deposited, and the liquid phase was colorless and transparent. |

As is obvious from the results shown in Table 2, with hot water at 60° C., BHET or the like was deposited, so that water could not be passed through the columns. Further, when the concentration of ethylene glycol was lower than 30%, a deposit may be produced and accumulated on the surface of the activated carbon bed. Therefore, the concentration of ethylene glycol used in the sweetening-off step of the activated carbon column and the ion exchange resin column is preferably not lower than 30%, more preferably not lower than 60%. In addition, it is understood that alcohols such as methanol and isopropanol are suitable as the displacement solvent.

In the method of purifying BHET or the like in which crude BHET or the like is purified by a combination of activated carbon and ion exchange resins, a regeneration step can be carried out stably by use of ethylene glycol or an alcohol as a displacement solvent.

Third Embodiment

Next, a third embodiment will be described. An overall process in the third embodiment is the same as those of the first and second embodiments, and description thereof will be omitted.

Ion exchange resins used in the above second embodiment were a strongly acidic cation exchange resin and a weakly basic anion exchange resin. When a capability of deionization is of primary importance, it is preferable to use a strongly basic anion exchange resin as an anion exchange resin. However, a solution passing temperature must be set to be 60° C. or higher depending on the concentration of a crude BHET or the like, and to carry out solution passing treatment at such high temperatures, use of a weakly basic anion exchange resin as an anion exchange resin is inevitable.

However, it has been found that when a weakly basic anion exchange resin is used, the amount of leakage of salts increases as the treatment is repeated and high-purity monomers cannot be recovered accordingly.

In the third embodiment, in a method of purifying a bishydroxyalkyl terephthalate in which a crude bishydroxyalkyl terephthalate was subjected to solution passing treatment by a combination of activated carbon and ion exchange resins to purify it, the crude bishydroxyalkyl terephthalate was passed through a mixed bed of a strongly acidic cation exchange resin and a weakly basic anion exchange resin after passage through a single bed of a strongly acidic cation exchange resin.

Although details on the types of ions in crude BHET obtained from a recovered PET bottle are not known, it has been found that the amount of leakage of salts decreases when the crude BHET is passed through a mixed bed of a strongly acidic cation exchange resin and a weakly basic anion exchange resin.

Further, although details on the concentration of ions in crude BHET obtained from a recovered PET bottle are not known, it has been found that more cation components are dissolved than anion components. Therefore, to remove excess cation components, the crude BHET was passed through a single bed of a strongly acidic cation exchange resin before passage through a mixed bed of a strongly acidic cation exchange resin and a weakly basic anion exchange resin, whereby the throughput amount of the treated solution per regeneration can be increased without degrading the quality of the treated solution.

The mixing ratio of a strongly acidic cation exchange resin and a weakly basic anion exchange resin in the mixed bed of the strongly acidic cation exchange resin and the weakly basic anion exchange resin is 2:1 to 1:4, preferably 1:1 to 1:2, in terms of volume.

Further, although a detailed removal mechanism for purifying crude BHET or the like is not revealed in the present invention, it has been found that colorants contained in crude BHET or the like are not adsorbed well on an ion exchange resin but adsorbed on activated carbon.

It is preferred that crude BHET or the like be dissolved in a solvent at a high temperature and treated. Illustrative examples of a solvent to be used include methanol, or ethylene glycol or the like which is used in the solvolysis of PET or the like.

The treatment with activated carbon and the treatment with the ion exchange resins may be carried out in any order. However, since elution of oxides occurs by passing the solution through the columns depending on the degree of purification by activated carbon, it is preferred to carry out the treatment with the ion exchange resins after the treatment with activated carbon is carried out.

(Examples About Third Embodiment)

A crude BHET solution used in Examples and Comparative Examples was a solution which was obtained by filtration after a process of chemically recycling a PET bottle and comprised 18 wt % of PET, 81 wt % of ethylene glycol and 1 wt % of water.

EXAMPLE 4

After a crude BHET solution was passed through an activated carbon bed filled with 100 ml of wood-based activated carbon ("TAIKO SGA" manufactured by Futamura Chemical Industries Co., Ltd.) at 60° C. and a solution passing flow rate of 250 ml/hr, the solution was passed through a single-bed of strongly acidic cation exchange resin (24 ml of "AMBERRITE IR-120B" manufactured by ROHM & HAAS COMPANY) and then passed through a mix-bed of ion exchange resins (12 ml of "AMBERRITE IRA96SB"+12 ml of "AMBERRITE IR-120B", both manufactured by ROHM & HAAS COMPANY). Conductivities of the treated solution when 1,000 ml, 2,000 ml and 3,000 ml of the crude BHET solutions were passed through the above beds are shown in Table 3.

Comparative Example 3

After a crude BHET solution was passed through an activated carbon bed filled with 100 ml of wood-based activated carbon ("TAIKO SGA" manufactured by Futamura Chemical Industries Co., Ltd.) at 60° C. and a solution passing flow rate of 250 ml/hr, the solution was passed through a single-bed of strongly acidic cation exchange resin (36 ml of "AMBERRITE IR-120B") layer and then passed through a single-bed of weakly basic anion exchange resin (12 ml of "AMBERRITE IRA96SB") layer. Conductivities of the treated solution when 1,000 ml, 2,000 ml and 3,000 ml of the crude BHET solutions were passed through the above layers are shown in Table 3.

Comparative Example 4

After a crude BHET solution was passed through an activated carbon bed filled with 100 ml of wood-based activated carbon ("TAIKO SGA" manufactured by Futamura Chemical Industries Co., Ltd.) at 60° C. and a solution passing flow rate of 250 ml/hr, the solution was passed through a mix-bed of ion exchange resins (12 ml of "AMBERRITE IRA96SB"+36 ml of "AMBERRITE IR-120B", both manufactured by ROHM & HAAS COMPANY). Conductivities when 1,000 ml, 2,000 ml and 3,000 ml of the crude BHET solutions were passed through the above beds are shown in Table 3.

TABLE 3

|  | Conductivity ($\mu$S/cm) | | |
| --- | --- | --- | --- |
|  | 1,000 ml | 2,000 ml | 3,000 ml |
| Example 1 | 0.94 | 1.13 | 1.34 |
| Comp. Example 3 | 1.34 | 2.88 | 12.0 |
| Comp. Example 4 | 2.54 | 2.88 | 3.02 |

As is obvious from the results shown in Table 3, in the purification method of Comparative Example 3 in which the crude BHET solution was passed through the single-bed of strongly acidic cation exchange resin and the single-bed of weakly basic anion exchange resin, salts started to leak when 2,000 ml of the crude solution was passed through the resins. In the purification method of Comparative Example 4 in which the crude BHET solutions were passed through the mix-bed of ion exchange resins comprising a strongly acidic cation exchange resin and a weakly basic anion exchange resin, salts started to leak when 1,000 ml of the crude solution was passed through the beds. On the other hand, in the purification method of Example 4 in which the crude BHET solution was passed through the single-bed of the strongly acidic cation exchange resin and then the mix-bed of ion exchange resins, it is understood that salts did not leak much even after 3,000 ml of the crude solution was passed through the beds.

In a method of purifying crude BHET or the like by use of a combination of activated carbon and ion exchange resins, the crude BHET or the like is passed through a single-bed strongly acidic cation exchange resin and then a mix-bed ion exchange resin layer comprising a strongly acidic cation exchange resin and a weakly basic anion exchange resin, whereby purification of the crude BHET or the like without a significant leakage of salts can be carried out.

Fourth Embodiment

Next, a fourth embodiment will be described. An overall process in the fourth embodiment is the same as those of the first, second and third embodiments, and description thereof will be omitted.

The efficiency of purification of bishydroxyalkyl terephthalate can be increased by the above embodiments. However, in these purification processes, when the performance of a filter in the preceding filtration is insufficient, the activated carbon treatment device and the ion exchange resin treatment device were clogged, whereby a differential pressure increased and solution passing treatment was not be able to be carried out.

In the fourth embodiment, in a method of purifying bishydroxyalkyl terephthalate in which filtered crude bishydroxyalkyl terephthalate was subjected to a combination of a treatment with activated carbon and a treatment with an ion exchange resins to purify it, filtration was carried out at a temperature higher than a temperature at which the crude bishydroxyalkyl terephthalate was passed through the activated carbon or the ion exchange resins by 5° C. or lower.

In the fourth embodiment, a pretreatment process was filtration. Although a filter used in the filtration is not particularly limited, it may be, for example, a diatomaceous earth filter, a precision filter or a hollow fiber filter. To remove most of SS (Suspended Solids) contained in the crude BHET solution, these filters should preferably be capable of removing solids having sizes larger than 5 $\mu$m.

The present invention prevents clogging at the time of a treatment with activated carbon or a treatment with ion exchange resins from occurring and carries out purification of crude BHET or the like efficiently by adjusting the temperature of filtration and the temperature of the treatment with activated carbon or the treatment with ion exchange resin(s). Although details on SS concentrations in crude BHET obtained from a recovered PET bottle are not known, it has been found that solubility of SS varies with temperatures. It has been found that when the temperature of the filtration does not exceed the temperature of the treatment with activated carbon or the treatment with ion exchange resins by at most 5° C., deposition of SS on an activated carbon treatment device or an ion exchange resin treatment device is minimized, and any increase in differential pressure at the time of passing the crude BHET solution through the activated carbon treatment device or ion exchange resin treatment device is suppressed.

That is, the present invention is characterized in that the filtration is carried out at a temperature which does not exceed the temperature of the treatment with activated carbon or the treatment with ion exchange resins by at most 5° C., preferably at a temperature not higher than the temperature of the treatment with activated carbon or the treatment with ion exchange resins.

Although varying depending on the concentration of crude BHET, the filtration must be carried out at 40 to 100° C., preferably 60 to 80° C., since a temperature at which the BHET dissolves at a temperature of about 40° C. or higher and a possible solution passing temperature should not exceed 100° C. in consideration of heat resistance of ion exchange resins.

The temperature at which the treatment with activated carbon or the treatment with ion exchange resin(s) is carried out must be lower than the temperature of the filtration by at most 5° C. When the treatment with activated carbon or the treatment with ion exchange resins is carried out at a temperature lower than the temperature of the filtration by more than 5° C., insoluble components are deposited in the activated carbon bed or beds of ion exchange resins, a differential pressure increases, and the efficiency of purification decreases undesirably. The filtration should more preferably be carried out at a temperature not higher than the temperature of the treatment with activated carbon or the treatment with ion exchange resins since a solution passing treatment can be carried out without a large increase in differential pressure. Further, when the filtration is carried out between the temperature at the time of passing the solution through activated carbon or ion exchange resins and a temperature higher than the temperature by 50° C. or lower, a white deposit appears in the activated carbon or ion exchange resin bed. However, a pressure loss does not increase significantly.

Although the type of activated carbon used in the treatment with activated carbon is not particularly limited, it may be, for example, "DIAHOPE 008" manufactured by MITSUBISHI CHEMICAL CORPORATION, "CAL" manufactured by TOYO KALGON K.K. or "TAIKO SGA" manufactured by Futamura Chemical Industries Co., Ltd. as a wood-based granular activated carbon. A method of carrying out the treatment with activated carbon is not particularly limited, and a solution to be treated should be passed through a column filled with activated carbon.

As ion exchange resins used in the treatment with ion exchange resins, a variety of a strongly acidic cation exchange resins, a weakly basic anion exchange resin and a strongly basic anion exchange resin can be used. Illustrative examples of the ion exchange resins include "IR-120B", "IRA-96SB" and "IRA-402BL" manufactured by ROHM & HAAS COMPANY. The ion exchange resins may be used in any of a single-bed form, a mix-bed form or a multiple-bed form.

The treatment with activated carbon and the treatment with the ion exchange resins may be carried out in any order. However, since elution of oxides occurs when passing the solution through the column depending on the degree of purification by activated carbon, it is preferred to carry out the treatment with the ion exchange resins after the treatment with activated carbon is carried out.

(Examples About Fourth Embodiment)

EXAMPLE 5

The particle size distribution in water of SS contained in a crude BHET solution (BHET: 23%, ethylene glycol: 76%, water: 1%) obtained by chemically recycling PET bottles was measured by a particle size distribution meter LS-230 manufactured by COALTER CO., LTD. The results are shown in Table 4.

TABLE 4

| SS Having A Size of 0 to 1.0 $\mu$m | 1 vol % |
| SS Having A Size of 0 to 2.9 $\mu$m | 5 vol % |
| SS Having A Size of 0 to 4.5 $\mu$m | 10 vol % |
| SS Having A Size of 0 to 8.8 $\mu$m | 25 vol % |
| SS Having A Size of 0 to 18.1 $\mu$m | 59 vol % |

As is obvious from the results shown in Table 4, it is understood that removal of SS having sizes of not smaller than 5 $\mu$m leads to removal of at least 90% of the SS.

Thus, in Example 5, a crude BHET solution (BHET: 23%, ethylene glycol: 76%, water: 1%) obtained by chemically recycling PET bottles was filtered by means of a filter having a pore size of 5 $\mu$m at 55° C.

Then, 20,000 ml of the filtered solution was passed through a column filled with 50 ml of activated carbon (trade name "DIAHOPE 008", manufactured by MITSUBISHI CHEMICAL CORPORATION) and a column filled with 50 ml of an ion exchange resin (trade name "IR-120B", manufactured by ROHM & HAAS CO., LTD.) at 65° C.

As a result, no white deposit appeared on the activated carbon, no increase in differential pressure was observed, and the solution passing treatments could be carried out stably.

Comparative Example 5

The crude BHET solution used in Example 5 was filtered by means of a filter having a pore size of 5 $\mu$m at 80° C.

Then, 20,000 ml of the filtered solution was passed through a column filled with 50 ml of activated carbon (trade name "DIAHOPE 008", manufactured by MITSUBISHI CHEMICAL CORPORATION) and a column filled with 50 ml of an ion exchange resin (trade name "IR-120B", manufactured by ROHM & HAAS CO., LTD.) at 65° C.

As a result, a white deposit was accumulated on the activated carbon, and a decrease in solution passing flow rate was observed along with an increase in differential pressure.

In a method of purifying crude BHET or the like by subjecting the crude BHET or the like to a treatment with activated carbon and a treatment with an ion exchange resin(s) after filtration, the filtration is carried out at a temperature not exceeding by 5° C. at which the treatment with activated carbon or the treatment with an ion exchange resin is carried out, whereby the treatment with activated carbon and the treatment with ion exchange resins can be carried out stably without an increase in differential pressure.

Fifth Embodiment

Figure 2:
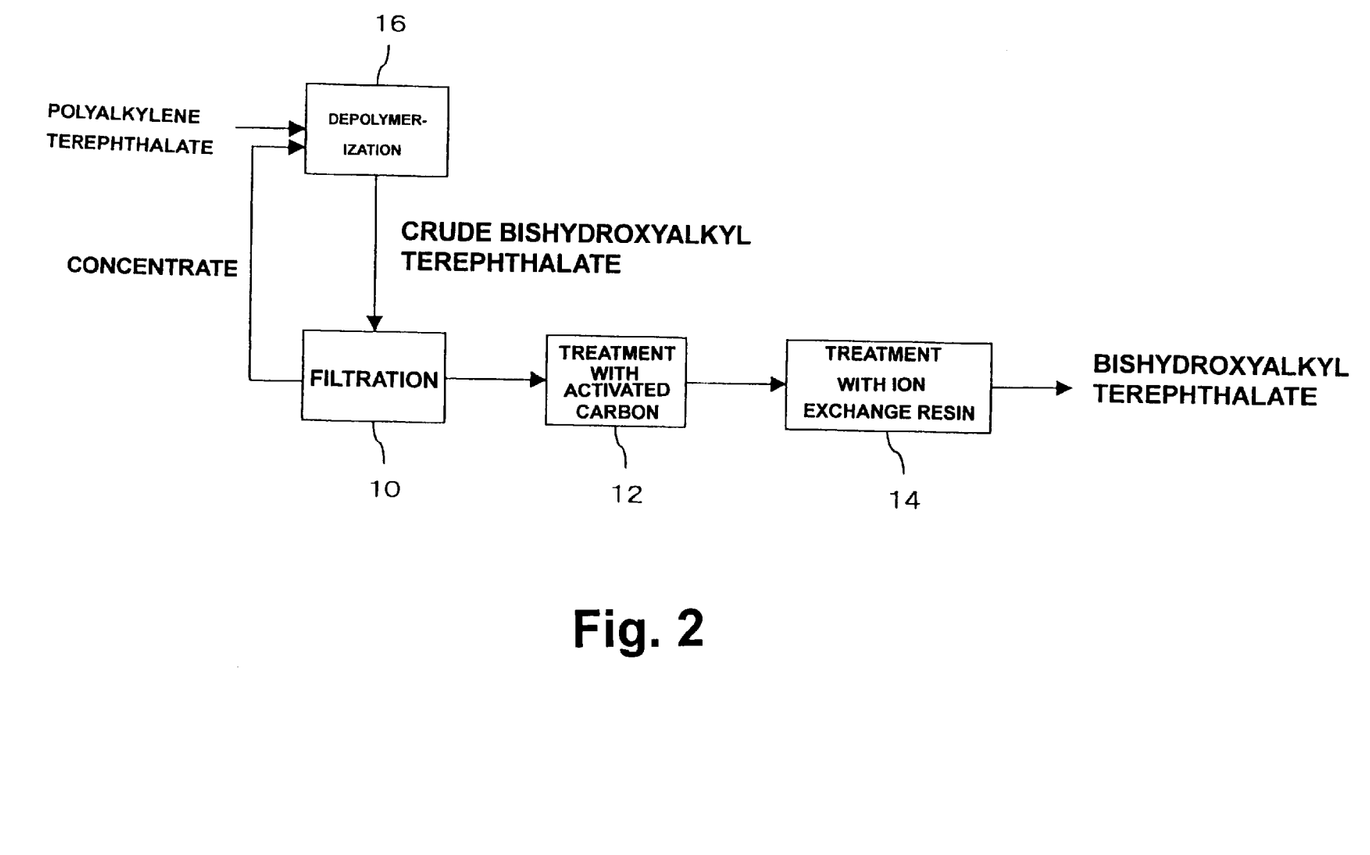
FIG. 2 is a diagram of showing the constitution of a fifth embodiment.

Next, a fifth embodiment will be described. As shown in FIG. 2, after subjected to pretreatment such as pulverization or washing, PET or the like is supplied to depolymerization 16. Then, crude bishydroxyalkyl terephthalate obtained in the depolymerization is subjected to filtration 10 and then subjected to an activated carbon treatment 12 and an ion exchange resin treatment 14. A concentrate separated by the filtration is returned to the depolymerization 16. The processes after the filtration 10 in the fifth embodiment are the same as those in the above fourth embodiment, and descriptions thereof will be omitted accordingly.

In the above embodiments, a concentrate separated by filtration as such had been discarded. However, when the condensate was analyzed, it was found that oligomers made from BHET etc. and pigment components are contained therein. Further, it was also found that no problem occurred even when crude BHET or the like in the concentrate was returned to the step where PET or the like was depolymerized through solvolysis by use of a solvent such as an alcohol or glycol in the presence of a catalyst.

The fifth embodiment comprised a depolymerization step in which polyalkylene terephthalate was subject to ester depolymerization to produce crude bishydroxyalkyl terephthalate and a purification step in which the obtained crude bishydroxyalkyl terephthalate was filtered and then purified and solids separated by the filtration in the above purification step were returned to the above depolymerization step.

That is, as shown in FIG. 2, after subjected to pretreatments such as pulverization and washing, PET or the like was supplied to the depolymerization 16 where a crude bishydroxyalkyl terephthalate was obtained from the PET or the like by an ester depolymerization reaction. The ester depolymerization is a reaction in which one molecule of ethylene glycol is reacted with one unit of PET (polyethylene terephthalate) to synthesize BHET (bishydroxyethyl terephthalate). Further, in the case of polybutylene terephthalate, the ester depolymerization is caused by use of 1,3-butanediol to obtain crude bishydroxybutyl terephthalate.

Then, the crude BHET or the like obtained by the ester depolymerization of the PET or the like is first filtered by the filtration 10. Thereafter, concentrate separated by the filtration is returned to the depolymerization 16. A filtrate obtained as a result of the filtration 10 is subjected to the activated carbon treatment 12 and the ion exchange treatment 14, thereby obtaining a purified bishydroxyalkyl terephthalate.

As described above, the crude BHET or the like obtained by ester depolymerization of the PET or the like are filtered. Although a filter used in the filtration is not particularly limited, it may be, for example, a diatomaceous earth filter, a precision filter or a hollow fiber filter. To remove most of SS (Suspended Solids) contained in a solution of crude BHET or the like, these filters are preferably capable of removing solids each having a size larger than 5 μm.

Although varying depending on the concentration of crude BHET, the filtration must be carried out at 40 to 100° C., preferably 60 to 80° C., since a temperature at which the BHET dissolves is not lower than about 40° C. and a possible solution passing temperature should not be higher than 100° C. in consideration of heat resistance of ion exchange resins.

The concentrate separated by the filtration contains oligomers made from BHET etc. and pigment components. No adverse effect is produced even if the concentrate is returned to the depolymerization step. That is, it has been found that the oligomers such as BHET is decomposed into soluble monomers by depolymerization and the pigment components do not inhibit the depolymerization reaction.

As the treatment with activated carbon and the treatment with an ion exchange resin, those in the above embodiments are suitably employed.

As activated carbon used in the activated carbon treatment and ion exchange resin(s), the same activated carbon and ion exchange resin(s) as those used in the above fourth embodiment are suitably employed.

(Example About Fifth Embodiment)

The particle size distribution in water of an SS component contained in a crude BHET solution (BHET: 23%, ethylene glycol: 76%, water: 1%) obtained by ester depolymerizing a PET bottle at a weight ratio of ethylene glycol and a PET of 4.9, a pressure of 0.1 MPa and a temperature of 200° C. for a reaction time of 3.8 hours was measured by a particle size distribution meter LS-230 (trade name) manufactured by COALTER CO., LTD. The results were the same as those shown in Table 4.

Then, the above BHET solution (BHET: 23%, ethylene glycol: 76%, water: 1%) was filtered by means of a filter having a pore size of 5 μm at 55° C.

Then, a concentrate deposited on the filter was collected. This concentrate was vacuum dried to remove water and ethylene glycol therefrom, thereby obtaining a dry concentrate.

What is claimed is:

1. A purification method of bishydroxyalkyl terephthalate in which crude bishydroxyalkyl terephthalate is purified, by treating it with activated carbon and ion exchange resins.

2. The method of claim 1, wherein the bishydroxyalkyl terephthalate is bishydroxyethyl terephthalate or bishydroxybutyl terephthalate.

3. The method of claim 1, wherein the crude bishydroxyalkyl terephthalate is dissolved in a solvent heated at 40 to 120° C. and treated with activated carbon and ion exchange resins.

4. The method of claim 1, wherein the ion exchange resins are an anion exchange resin and a cation exchange resin.

5. The method of claim 4, wherein the temperature of the crude bishydroxyalkyl terephthalate when treated with the ion exchange resins is not lower than 70° C. and the anion exchange resin is a weakly basic anion exchange resin.

6. The method of claim 1, wherein the crude bishydroxyalkyl terephthalate is obtained by solvolysis of waste polyethylene terephthalate or waste polybutylene terephthalate.

7. The method of claim 1, wherein the activated carbon is wood-based activated carbon.

8. The method of claim 1, wherein the treatment with the activated carbon and the ion exchange resins comprises:

a solution passing step of passing a solution containing the crude bishydroxyalkyl terephthalate through an activated carbon column filled with the activated carbon and an ion exchange resin column filled with the ion exchange resins, and a sweetening-off step of passing ethylene glycol or an alcohol through each of the columns after the solution passing step to displace bishydroxyalkyl terephthalate.

9. The method of claim 8, wherein the alcohol is methanol.

10. The method of claim 8, wherein the bishydroxyalkyl terephthalate is bishydroxyethyl terephthalate or bishydroxybutyl terephthalate.

11. The method of claim 8, wherein the crude bishydroxyalkyl terephthalate is dissolved in a solvent heated at 40 to 120° C. and treated with the activated carbon and the ion exchange resins.

12. The method of claim 8, wherein the concentration of ethylene glycol or alcohol which is passed through the columns is not lower than 30%.

13. The method of claim 1, wherein the treatment with activated carbon and ion exchange resins comprises:

a solution passing step of passing a solution containing the crude bishydroxyalkyl terephthalate through an activated carbon column filled with the activated carbon and an ion exchange resin column filled with the ion exchange resins, and a regeneration step of regenerating the ion exchange resins after the solution passing step, and the regeneration step comprises:

a sweetening-off step of passing ethylene glycol or an alcohol as a solvent through the columns to displace bishydroxyalkyl terephthalate, a rinsing step of rinsing the ion exchange resins with water after the sweetening-off step, a chemical regeneration step of passing regenerant chemicals through the ion exchange resins to regenerate the ion exchange resins after the rinsing step, another rinsing step of rinsing the ion exchange resin with water after the chemical regeneration step, and a displacement step of passing ethylene glycol or an alcohol through the ion exchange resins to displace water remaining in the ion exchange resins with ethylene glycol or the alcohol after the preceding rinsing step.

14. The method of claim 1, wherein the treatment with ion exchange resins comprises:

a step of passing the crude bishydroxyalkyl terephthalate through a single bed of a strongly acidic cation exchange resin, and a step of passing the crude bishydroxyalkyl terephthalate through a mixed bed of a strongly acidic cation exchange resin and a weakly basic anion exchange resin.

15. The method of claim 14, wherein the bishydroxyalkyl terephthalate is bishydroxyethyl terephthalate or bishydroxybutyl terephthalate.

16. The method of claim 1, which further comprises a filtration step which is carried out before the treatment with activated carbon and ion exchange resins at a temperature not exceeding by 5° C. at which the treatment with activated carbon and ion exchange resins is carried.

17. The method of claim 16, wherein the bishydroxyalkyl terephthalate is bishydroxyethyl terephthalate or bishydroxybutyl terephthalate.

18. The method of claim 16, wherein the filtration is carried out at a temperature not higher than a temperature at which the treatment with activated carbon and ion exchange resins is carried out.

19. The method of claim 16, wherein the filtration is carried out at 10 to 100° C.

20. The method of claim 16, wherein the filtration is carried out by use of a filter capable of separating solids having a particle diameter of not smaller than 5 μm.

21. A purification method of bishydroxyalkyl terephthalate, which comprises:
- a depolymerization step of subjecting polyalkylene terephthalate to ester depolymerization to produce crude bishydroxyalkyl terephthalate, and
- a purification step of filtering the obtained crude bishydroxyalkyl terephthalate to purify it, and
- returns solids separated by the filtration in the purification step to the depolymerization step.

22. The method of claim 21, wherein the polyalkylene terephthalate is polyethylene terephthalate or polybutylene terephthalate.

23. The method of claim 21, wherein the bishydroxyalkyl terephthalate is bishydroxyethyl terephthalate or bishydroxybutyl terephthalate.

24. The method of any one of claim 21, wherein the filtration is carried out at 40 to 100° C.

25. The method of any one of claim 21, wherein the filtration is carried out by use of a filter capable of separating solids having a particle diameter of not smaller than 5 μm.

26. The method of any one of claim 21, wherein the purification step includes a treatment with a combination of activated carbon and ion exchange resins.

* * * * *